United States Patent [19]

Thurin et al.

[11] Patent Number: 4,849,509

[45] Date of Patent: Jul. 18, 1989

[54] MONOCLONAL ANTIBODIES AGAINST MELANOMA-ASSOCIATED ANTIGENS AND HYBRID CELL LINES PRODUCING THESE ANTIBODIES

[75] Inventors: Jan Thurin, Philadelphia; Hilary Koprowski; Meenhard Herlyn, both of Wynnewood; Zenon Steplewski, Malvern, all of Pa.

[73] Assignee: The Wistar Institute, Philadelphia, Pa.

[21] Appl. No.: 16,902

[22] Filed: Feb. 20, 1987

[51] Int. Cl.$^4$ .................. A61K 39/395; C12N 15/00; C07K 15/04

[52] U.S. Cl. .................. 530/387; 530/389; 530/806; 530/828; 424/85.8; 435/68; 435/172.2; 435/172.3; 435/240.27

[58] Field of Search .............. 530/387, 388, 389, 391, 530/806, 828; 424/85, 85.8; 435/68, 172.2, 240.27, 240.26

[56] References Cited

U.S. PATENT DOCUMENTS

| | | | |
|---|---|---|---|
| 4,172,124 | 10/1979 | Koprowski et al. | |
| 4,444,744 | 4/1984 | Goldenberg | 424/85 |
| 4,507,391 | 3/1985 | Pukel et al. | 435/68 |
| 4,562,160 | 12/1985 | Real et al. | 530/389 |
| 4,590,071 | 5/1986 | Scannon et al. | 530/391 |
| 4,591,572 | 5/1986 | Mattes et al. | 424/85 |
| 4,649,115 | 3/1987 | Safai et al. | |
| 4,675,287 | 6/1987 | Reisfeld et al. | 530/387 |
| 4,693,966 | 9/1987 | Houghton et al. | 530/387 |

FOREIGN PATENT DOCUMENTS

86/00909  2/1986  PCT Int'l Appl. .

OTHER PUBLICATIONS

Pukel et al., J. Exp. Med., 155, 1133-47, (1982).
Dippold et al., Cancer Res., 45, 3699-705, (1985).
Cheresh et al., Cancer Res., 46, 5112-18, (Oct. 1986).
Natoli et al., Cancer Res., 46, 4116-20, (1986, Aug.).
Munro, Nature, 312, 597, (1984).
Sun et al., Hybridoma, 5(51), 517-20, 1986.
Spira et al., J. Imm. Met., 74, 307-15, (1984).
Steplewski et al., PNAS (U.S.A.), 82, 8653-7, (1985).
Cheresh et al., PNAS (U.S.A.), 81, 5767-71, (1984).
Kundu et al., Bioch. Biophys. Res. Comm., 116(3), 836-42, (1983).
Cheresh et al., PNAS, 82, 5155-9, (1985).
Houghton et al., PNAS (U.S.A.), 82, 1242-6, (1985).
Hellström et al., PNAS (U.S.A.), 82, 1499-1502, (1985).
Thurin et al., J. Biol. Chem., 260 (27), 14556-63, (1985).
Localization of the Gangliosides $GD_2$ and $GD_3$ in Adhesion Plaques and on the Surface of Human Melanoma Cells, Cheresh, Harper, Schulz & Reisfeld, Proc. Natl. Acad. Sci., U.S.A., vol. 81, pp. 5767-5771, Sep. 1984, Cell Biology.
Strong Antitumor Activities of $IgG_3$ Antibodies to a Human Melanoma-Associated Ganglioside, Hellstrom, Brankovan and Hellstrom, Department of Microbiology and Immunology, University of Washington, Seattle, Wash., Proc. Natl. Acad. Sci., U.S.A., vol. 82, pp. 1499-1502, Mar. 1985, Immunology.
$GD_3$, A Prominent Ganglioside of Human Melanoma—Detection and Characterization by Mouse Monoclonal Antibody, Pukel, Lloyd, Travassos, Dippold, Oettgen & Old, Memorial Sloan-Kettering Cancer Center, New York, J. Exp. Med. Vol. 155, Apr., 1982.
A Monoclonal Antibody Recognizes an O-Acylated Sialic Acid in a Human Melanoma-Associated Ganglioside, Cheresh, Varki, Stallcup, Levine & Reisfeld, The Journal of Biological Chemistry, vol. 295, No. 12, Issue of Jun. 25, pp. 7453-7459, 1984.
*Identification of a Human Neuroectodermal Tumor Antigen (OFA-I-2) as Ganglioside GD2*, Leslie D. Cahan et al., Proc. Natl. Acad. Sci., vol. 79, pp. 7629-7633, Dec., 1982.
Human Antibody to OFA-I, a Tumor Antigen, Produce in vitro by Epstein-Barr Virus-Transformed Human B-Lymphoid Cell Lines, Reiko F. Irie et al., Proc. Natl. Acad. Sci., U.S.A., vol. 79, pp. 5666-5670, Sep., 1982.
*Detection of Ganglioside $GD_2$ in Tumor Tissues and Sera of Neuroblastoma Patients*, Gregor Schulz et al., Cancer Research, 44, 5914-5920, Dec. 1984.

Primary Examiner—Margaret Moskowitz
Assistant Examiner—Jeff P. Kushan
Attorney, Agent, or Firm—Banner, Birch, McKie & Beckett

[57] ABSTRACT

The present invention is directed to monoclonal antibodies, and hybridomas which produce them, which are reactive with ganglioside antigens GD2 and GD3 and are essentially non-reactive with other ganglioside antigens. The invention further relates to methods of using these antibodies.

5 Claims, 3 Drawing Sheets

MONOCLONAL ANTIBODIES AGAINST MELANOMA-ASSOCIATED ANTIGENS AND HYBRID CELL LINES PRODUCING THESE ANTIBODIES

BACKGROUND OF THE INVENTION

1. Field of the Invention

This invention is directed to monoclonal antibodies against ganglioside antigens associated with melanoma, hybrid cell lines producing these antibodies, and methods of using these monoclonal antibodies.

2. Description of the Background Art

Gangliosides are a major class of carbohydrate-rich glycolipids of extremely large size and complexity. Gangliosides are usually found on the outer surface of cell membranes, especially among the cells of the nervous system. It has been suggested that gangliosides may function as membrane receptors for growth factors, hormones, and adhesion molecules. In recent years, the possible role of gangliosides as tumor markers has received considerable attention. As a result, investigators have produced monoclonal antibodies which specifically react with gangliosides on the surface of human melanoma (Cheresh, et al., *Proceedings of the National Academy of Sciences, U.S.A.*, 82:5155, 1985; Cheresh, et al., *Proceedings of the National Academy of Sciences, U.S.A.*, 81:5767, 1984; Pukel, et al., *Journal of Experimental Medicine*, 155:1133, 1982; Cheresh, et al., *Journal of Biological Chemistry*, 259:7453, 1984), neuroblastoma (Schulz, et al., *Cancer Research*, 44:5914, 1984), and colon carcinoma (Koprowski, et al., *Somatic Cell Genetics*, 5:957–972, 1979). Several recent studies have pointed to ganglioside antigen GD3 as being a potential target for immunotherapy in human melanoma (Hellstrom, et al., *Proceedings of the National Academy of Sciences, U.S.A.*, 82:1499, 1985). Previous studies had identified ganlisodie antigen GD2 as another melanoma-associated antigen.

Although ganglioside antigens are present in central nervous tissue, GD2 is greatly enriched in melanoma, brain tumors, neuroblastoma, small cell carcinoma of the lung and other tumors of neuroectodermal origin. Studies on the development of these ganglioside antigens indicate that GD3 is a precursor of GD2 and that the distribution of GD2 and GD3 in various melanomas varies depending upon the severity of the disease. In general, ganglioside antigen GD2 occurs primariliy in advanced primary and metastatic melanoma and is rarely present in normal tissue.

At present the method of choice for the treatment of melanoma and other tumors bearing ganglioside antigens GD2 and GD3 involves excision of the involved malignant tissue. Unfortunately, in advanced stages the accompanying deep tissue invasion by the tumor makes this approach much more difficult due to the increase in surgical trauma and the amount of tissue that may be excised. Since the survival rate of malignant melanoma is inversely related to the level of invasion of the host tissue present clinical strategy has no choice but to resort to surgery. However, in advanced stages the increased dissemination of the tumor creates a situation in which surgical excision is much less likely to be successful. Consequently, this results in a greatly reduced prognosis for those patients having advanced malignancies.

SUMMARY OF THE INVENTION

It is an object of the present invention to provide a monoclonal antibody that is capable of reacting with both GD2 and GD3, for purposes of effective diagnosis and therapy of neoplastic disease expressing these antigens.

Another object of the present invention is to produce monoclonal antibodies that are capable of reacting with both ganglioside atigen GD2 and GD3, but show much greater reactivity towards GD2 than GD3 and essentially no reactivity with other ganglioside antigens such as GQ 1b.

It is another object of the present invention to provide methods for the in vitro and in vivo diagnosis of malignancies using monoclonal antibodies which react with ganglioside antigens GD2 and GD3.

Still another object of the invention is to provide methods for suppressing malignant disease in an animal using unlabeled or therapeutically labeled monoclonal antibodies which react with ganglioside antigens GD2 and GD3.

The present invention thus relates to new monoclonal antibodies specific for ganglioside antigens GD2 and GD3 but are essentially non-reactive with other ganglioside antigens such as GQ 1b. The invention further includes hybrid cell lines which produce these antibodies as well as methods of using and processes of preparing these monoclonal antibodies.

The ability to react with both gangliosides while at the same time remaining essentially non-reactive with gangliosides such as GQ 1b which is present in normal fibroblasts, is very significant in terms of the detection of these antigens and the immunotherapeutic use of these monoclonal antibodies. Since tumors vary with respect to their expressions of GD2 and GD3, that is, some tumors express only one or the other of these ganglioside antigens whereas other tumors express both, the ability to react with both of these antigens is of obvious clinical importance. On the other hand, the fact that the monoclonal antibodies in one embodiment of the invention are preferentially reactive with ganglioside antigen GD2 is important since GD2, unlike GD3 which is also present in normal skin, is found much less frequently on normal tissue. Thus, the monoclonal antibodies of the invention demonstrate a level of specificity for malignant tissue heretofore not seen.

Filled circles and squares indicate GD2 and GD3 gangliosides, respectively, detected with monoclonal antibody of IgG2a (ME 361-S2a) isotype and open circles and squares with IgG3 (ME 361) isotype. The filled triangle indicates reactivity with gangliosides GM4, GM3, GM2, GM1, GD1a, GD1b, GT1a, GQ1b, and disialoparagloboside (III$^2$(NeuAc)$_2$nLc$_4$Cer) as detected with both IgG2a and IgG3 isotypes.

FIG. 2.

(A) Thin layer chromatography of total ganglioside fractions from Wistar melanoma (WM) cell cultures: (1) WM 75, (2) WM 373, (3) WM 115, (4) WM 266-4, (5) WM 239-A, (6) WM 165-1, (7) WM 278, (8) WM 46, (9) WM 164, (10) WM 9, and (11) SK MEL 23.

(B) Autoradiogram, developed for 20 hours, of the same fractions as in (A) above.

(C) Autoradiogram, developed for 20 hours, of the same fractions as in (A) treated with 0.1M KOH in methanol. All fractions were diluted relative to the protein content of the extracted cells and correspond to approximately 50 ug of ganglioside/lane.

Figure 3:
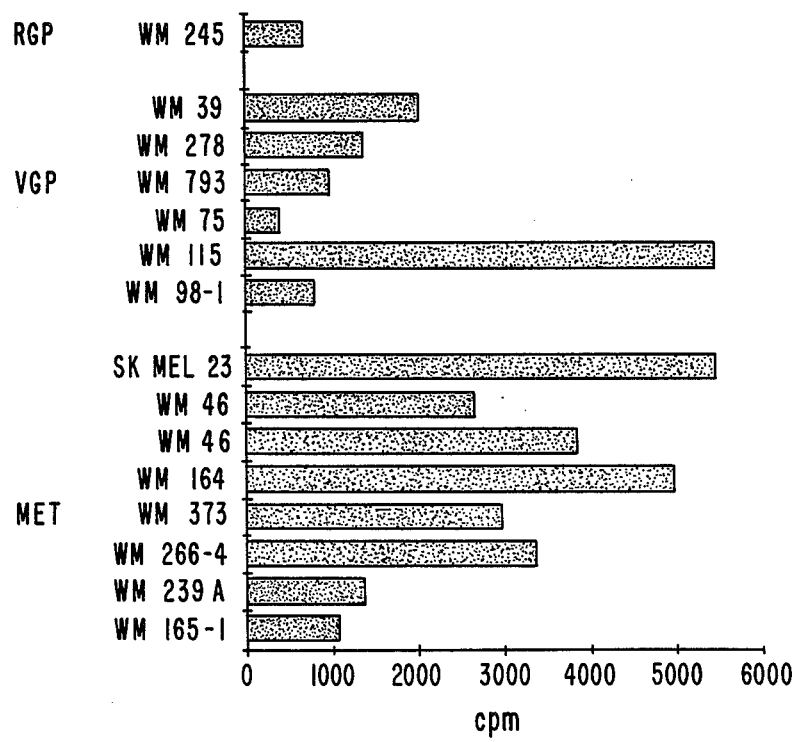

FIG. 3. Chart showing binding of monoclonal antibody ME 361 of gamma-3 isotype (ME 361) to serum-free culture supernatants of the indicated cell types. The cell cultures were grouped according to the type of lesion from which they were derived: radial growth phase melanoma (RGP), vertical growth phase melanoma (VGP) and metastatic melanoma (MET).

DESCRIPTION OF THE PREFERRED EMBODIMENTS

The present invention relates to monoclonal antibodies with specificity for antigens indicative of melanoma as well as other tumors such as for example, brain tumors, neuroblastoma, small cell carcinoma of the lung and, generally, any tumor of neuroectodermal origin. These monoclonal antibodies are highly useful for both the in vitro and in vivo immunological detection of ganglioside antigens commonly associated with these tumors and for the immunotherapy of tumors bearing these ganglioside antigens.

The general method used for production of hybridomas secreting monoclonal antibodies is well known to those or ordinary skill in the art. Illustrative of the techniques utilized in the present invention are those described in *Proceedings of the National Academy of Science, USA,* 75: 3405, (1978) and Koprowski, U.S. Pat. No. 4,172,124 entitled "Method of Producing Tumor Antibodies."

Briefly, BALB/mice were immunized with cultured metastatic melanoma cells (SK MEL 23) and later boosted with the same cell line. After three days, the animals were sacrificed and the spleen cells were fused with the 653 variant of mouse myeloma P3X63 Ag8. The resulting hybridomas were screened for production of monoclonal antibodies and tested for specificity using various melanoma and cancer cell cultures. In addition, a class-switch variant was produced and isolated using known techniques (Steplewski, et al., *Proceedings of the National Academy of Sciences, U.S.A.,* 82: 8653, 1985).

The isolation of other hybridomas screening monoclonal antibodies with the specificity of the monoclonal antibodies of the invention can be accomplished by one of ordinary skill in the art by the technique of anti-idiotypic screening (Potocnjak, et al., *Science,* 215:1637, 1982). Briefly, an anti-idiotypic antibody is an antibody which recognizes unique determinants present on the antibody produced by the hybridoma of interest. The anti-idiotypic antibody is prepared by immunizing an animal, as was used as the source of the monoclonal antibody, with the monoclonal antibody of interest. The animal immunized will recognize and respond to the idiotypic determinants of the immunizing antibody by producing an antibody to these idiotypic determinants. By using the antibodies of the second animal, which are specific for the monoclonal antibodies produced by a single hybridoma, it is now possible to identify other clones with exactly the same idiotype as the antibody of the hybridoma used for immunization. Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity. In antibodies, these idiotypic determinants are present in the hypervariable region which binds to a given epitope.

The present invention is directed to monoclonal antibodies, and hybridomas which produce them, which are reactive with ganglioside antigens GD2 and GD3 and are essentially non-reactive with other ganglioside antigens. It can easily be determined whether a monoclonal antibody has the requisite specificity by performing an antigen binding immunoassay such as the ELISA and RIA described in Example 2 infra.

Alternatively, since the inventors have characterized an epitopic moiety to which monoclonal antibodies having the specificity of those of the invention react, it is now a matter of routine skill to produce more hybridomas secreting monoclonal antibodies of identical epitopic specificity. The saccharide portion of the purified GD-2 ganglioside, which binds the monoclonal antibodies of the invention, can be purified from the major portion of GD-2 by such techniques as ozonolysis (Sabesan, et al., *Canadian Journal of Chemistry,* 62: 1034, 1984) or by specific enzymatic hydrolysis as with endoglyceroceramidase (Ito, et al., *Journal of Biological Chemistry,* 261: 14278, 1986). Thus, additional hybridomas secreting monoclonal antibodies having the specificity of monoclonal antibodies produced by cell lines ME 361 (ATCC HB 9325) and ME 361-S2a (ATCC HB 9326) can be produced for example, by coupling this epitope to an inert or immunogenic carrier molecule, such as KLH, to present the epitope in immunogenic form. (Hudson & Hay, *Practical Immunology,* p. 5–8, Blackwell Scientific Publications, 1980). In this manner, animals can be first immunized with whole malignant cells for initial sensitization followed by the epitope conjugate, or purified antigen alone, in the booster immunization to stimulate outgrowth of the preferred B-cell clones. In so doing, it is possible to greatly restrict the repertoire of responder B-cell clones which are present for hybridoma fusion and thereby avoid undue experimentation in isolating hybridomas of the desired specificity. After fusion, the hybridomas are screened using the epitope and free carrier to select those clones producing monoclonal antibodies which are specific for this epitope.

While the use of a foreign donor monoclonal antibody of one species in a second recipient species is usually not a factor in in vivo immunotherapy or immunodiagnosis, a potential problem which may arise is the occurrence of an adverse immunological response by the host to antigenic determinants present on the donor antibody. In some instances, this adverse response can be so severe as to curtail the in vivo use of the donor antibody in the host. Further, this adverse host response may serve to hinder the malignancysuppressing efficacy of the donor antibody. One way in which it is possible to circumvent the likelihood of an adverse immune response occuring in the host is by using chimeric antibodies (Sun, et al., *HYBRIDOMA,* 5(Supplement 1): S17, 1986; Oi, et al., *Bio Techniques,* 4(3): 214, 1986). Chimeric antibodies are antibodies in which the various domains of the antibody heavy and light chains are coded for by DNA from more than one species. Typically, a chimeric antibody will comprise the variable domains of the heavy ($V_H$) and light ($V_L$) chains derived from the donor species producing the antibody of desirable antigenic specificity and the constant antibody domains of the heavy ($C_H$) and light ($C_L$) chains derived from the host recipient species. It is believed that by reducing the exposure of the host immune system to the antigenic determinants on the door antibody domains the possibility of an adverse immunological response occuring in the recipient species will be reduced. Thus, for example, it is possible to produce a chimeric antibody for in vivo clinical use in humans which comprises mouse $V_H$ and $V_L$ domains coded for by DNA isolated from ME 361 (ATCC HB 9325) or ME 361-S2a (ATCC HB 9326) and $C_H$ and $C_L$ domains coded for by DNA isolated from a human cell.

Under certain circumstances monoclonal antibodies of one isotype might be more preferable than those of another in terms of their diagnostic or therapeutic efficacy. For example, it is known that mouse monclonal antibodies of isotype gamma-2a and gamma-3 are more effective in inhibiting the growth tumors than is the gamma-1 isotype. This differential efficacy is thought to be due to the ability of the gamma-2a and gamma-3 isotypes to more actively participate in cytolytic destruction of tumor cells. Particular isotypes of a monoclonal antibody can be prepared either directly by selecting from the initial hybridoma fusion or prepared secondarily from a parental hybridoma secreting a monoclonal antibody of different isotype by using the sib selection technique to isolate class-switch variants. (Steplewski, et al., *Proceedings of the National Academy of Sciences, USA*, 82:8653, 1985; Spira, et al., *Journal of Immunological Methods*, 74:307, 1984). Thus, the monoclonal antibodies of the invention would include class-switch variants having the specificity of monoclonal antibody ME361 which is produced by ATCC HB 9325 or ME 361-S2a which is produced by ATCC HB 9326.

The monclonal and chimeric antibodies of the invention can be used in any animal in which it is desirable to administer in vitro or in vivo immunodiagnosis or immunotherapy. The term "animal" as used herein is meant to include both humans as well as non-humans.

The term "antibody" as used in this invention is meant to include intact molecule as well as fragments thereof, such as, for example, Fab and F(ab')$_2$, which are capable of binding the epitopic determinant.

The term "essentially non-reactive" when used to characterize the reactivity between the monoclonal antibodies of the invention and an antigen means that any reaction which might occur is insignificant in terms of limiting the diagnostic or therapeutic usefulness of the antibodies.

The monoclonal antibodies of the invention are particularly suited for use in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such common immunoassays are the radioimmunoassay (RIA) and sandwich (immunometric) assay. Detection of the antigens using the monoclonal antibodies of the invention can be done utilizing immunoassays which are run in either the forward, reverse, or simultaneous modes, including immunohistochemical assays on physiological samples.

There are many carriers to which the monoclonal antibodies of the invention can be bound and which can be used in detecting the presence of melanoma-associated antigen. Well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibody, or will be able to ascertain such, using routine experimentation.

There are many different labels and methods of labeling known to those of ordinary skill in the art. Examples of the types of labels which can be used in the present invention include enzymes, radioisotopes, fluorescent compounds, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, the melanoma-associated antigen which is detected by the monoclonal antibodies of the invention may be present in biological fluids and tissues. Any sample containing a detectable amount of melanoma-associated antigen can be used. Normally, a sample is a liquid such as urine, saliva, cerebrospinal fluid, blood, serum and the like, or a solid or semi-solid such as tissues, feces, and the like.

Another technique which may also result in greater sensitivity consists of coupling the antibodies to low molecular weight haptens. These haptens can be specifically detected by means or a second reaction. For example, it is common to use such haptens as biotin, which reacts with avidin, or dinitrophenyl, pyridoxal, and fluoresceine, which can react with specific anti-hapten antibodies.

As used in this invention, the term "epitope" is meant to include any determinant capable for specific interaction with the monoclonal antibodies of the invention. Epitopic determinants usually consist of chemically active surface groupings of molecules such as amino acids or sugar side chains and usually have specific three dimensional structural characteristics, as well as a specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the ganglioside antigens for which the monoclonal antibodies are specific. The concentration of detectably labeled monoclonal antibody which is administered should be sufficient that the binding to the tumor site is detectable compared to the background signal. Further, it is desirable that the detectably labeled monoclonal antibody be rapidly cleared from the circulatory system in order to give the best tumor-to-background signal ratio.

As a rule, the dosage of detectably labled monoclonal antibody for diagnosis will vary depending on such factors as age, sex and extent of disease of the individual. The dosage of monoclonal antibody can vary from 0.01 mg/kg to 2000 mg/kg, preferably 0.1 mg/kg to 1000 mg/kg.

For diagnostic in vivo imaging, the type of detection instrument available is a major factor in selecting a given radioisotope. The radioisotope chosen must have a type of decay which is detectable for a given type of instrument. Still another important factor in selecting radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobin either directly or indirectly by using an intermediate functional group. Intermediate functional groups which often are used to bind radioistopes which exist as metallic ions to immunoglobins are the bifunctional chelating agents diethylenetriaminepentaacetic acid (DTPA) and ethylenediaminetetraacetic acid (EDTA).

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be used. Usually gamma and position emitting radioisotopes are used for camera imaging and paramagnetic isotopes for NMR.

The monoclonal antibodies of the invention can be used to monitor the course of malignant disease in an individual. Thus, by measuring the increase or decrease in the size or number of malignant sites, or changes in the concentration of antigen shed into various body fluids, it would be possible to determine whether a particular therapeutic regimen aimed at ameliorating the malignancy is effective.

The monoclonal antibodies of the invention can also be used, alone or in combination with effector cells (Douillard, et al., *Hybridoma*, 5 (Supp. 1): S139, 1986), for immunotherapy in an animal having a tumor which expresses malignancy-associated gangliosides with epitopes reactive with the monoclonal antibodies of the invention. When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231: 148, 1986) and can be selected to enable drug release from the monoclonal antibody molecule at the target site. Examples of therapeutic agents which can be coupled to the monoclonal antibodies of the invention for immunotherapy are drugs, radioisotopes, immunomodulators, lectins and toxins.

The drugs which can be conjugated to the monoclonal antibodies of the invention include non-proteinaceous as well as proteinaceous drugs. The term "non-proteinaceous drugs" encompasses compounds which are classically referred to as drugs such as for example, mitomycin C, daunorubicin, and vinblastine.

The proteinaceous drugs with which the monoclonal antibodies of the invention can be labeled include immunomodulators and other biological response modifiers. The term "biological response modifiers" is meant to encompass substances which are involved in modifying the immune response in such manner as to enhance the destruction of the ganglioside bearing tumor for which the monoclonal antibodies of the invention as specific. Examples of immune response modifiers include such compounds as lymphokines. Examples of lymphokines include tumor necrosis factor, interleukins 1, 2, and 3, lymphotoxin, macrophage activating factor, migration inhibition factor, colony stimulating factor and interferon. Interferons with which the monoclonal antibodies of the invention can be labeled include alpha-interferon, beta-interferon, and gamma-interferon and their subtypes.

In using radioisotopically conjugated monoclonal antibodies of the invention for immunotherapy certain isotopes may be more preferable than others depending on such factors as tumor distribution and mass as well as isotope stability and emission. If desired, the tumor distribution and mass can be evaluated by the in vivo diagnostic techniques described supra. Depending on the type of malignancy present some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}Y$, may be preferable. On the other hand if the malignancy consists of single target cells, as in the case of leukemia, a short range, high energy alpha emitter such as $^{212}Bi$ may be preferred. Examples of radioisotopes which can be bound to the monoclonal antibodies of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$.

Lectins are proteins, usually isolated from plant material, which bind to specific sugar moieties. Many lectins are also able to agglutinate cells and stimulate lymphocytes. Ricin is a toxic lectin which has been used immunotherapeutically. This is accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheriae* which can be used in this manner. This toxin consists of an alpha and beta subunit which under proper conditions can be separated. The toxic A component can be bound to antibody and used for site specific delivery to a tumor expressing the ganglioside antigens for which the monoclonal antibodies of the invention are specific.

Other therapeutic agents which can be coupled to the monoclonal antibodies of the invention are known, or can be easily ascertained, by those of ordinary skill in the art.

It is also possible to utilize liposomes with the monoclonal antibodies of the invention in their membrane to specifically deliver the liposome to the area of the tumor expressing ganglioside antigens GD2 or GD3. These liposomes can be produced such that they contain, in addition to the monoclonal antibody, such immunotherapeutic agents as those described above which would then be released at the tumor site (Wolff, et al., *Biochemica et Biophysica Acta*, 802: 259, 1984).

The dosage ranges for the administration of the monoclonal antibodies of the invention are those large enough to produce the desired effect in which the symptoms of the ganglioside expressing tumor are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications, immune tolerance or similar conditions. Dosage can vary from 0.1 mg/kg to 2000 mg/kg, preferably 0.1 mg/kg to 2000 mg/kg/dose, in one or more dose administrations daily, for one or several days. The antibodies can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic-/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention also relates to a method for preparing a medicament or pharmaceutical composition comprising the monoclonal antibodies of the invention, the medicament being used for therapy of tumors expressing the ganglioside antigens reactive with the monoclonal antibodies of the invention.

Monoclonal antibody can be utilized in the present invention. Me 361 is obtained from, or has the identifying characteristics of, an antibody obtained from the cell line having ATCC accession number HB 9325. Me 361-S2a is obtained from, or has the identifying characteristics of, an antibody obtained from the cell line having ATCC accession number HB 9326. These cell lines were placed on deposit for 30 years at the American Type Culture Collection (ATCC) in Rockville, Md. prior to February 19, 1987.

The above disclosure generally describes the present invention. A more complete understanding can be obtained by reference to the following specific examples which are provided herein for purposes of illustration only, and are not intended to limit the scope of the invention.

EXAMPLE 1

PREPARATION OF HYBRIDOMA CELL LINES PRODUCING MONOCLONAL ANTIBODIES TO MELANOMA-ASSOCIATED ANTIGENS

A. Tissues and Cells

The origin and maintenance of the majority of the melanoma cell cultures and other cell lines have been described (Herlyn, et al., *Journal of the National Cancer Institute*, 74:283, 1985; Herlyn, et al., *Cancer Investigation*, 1:215, 1983; Clark, et al., *Human Pathology*, 15:1147, 1985). The origin and ganglioside content of the cell cultures used are shown in Table 1.

TABLE 1

| | ORIGIN AND GD2 AND GD3 CONTENT OF SELECTED MELANOMA CELL CULTURES | | | |
|---|---|---|---|---|
| Patients | A | B | C | D |
| Primary (VGP) | WM 75 (GD2) | WM 115 (GD2 + GD3) | — | — |
| Metastatic (MET) | WM 373 (GD3) | WM 266-4 (GD2 + GD3) | WM 164 (GD3) | SK MEL 23 (GD2 + GD3) |

Tissues were obtained and prepared as described by Thurin, et al. (*Journal of Biological Chemistry*, 260:14556, 1985). Lymphocytes and monocytes were obtained from heparinized human peripheral blood by centrification on a Ficoll-Hypaque density gradient whereafter separation of adherent cells (monocytes) and non-adherent cells (lymphocytes) using plasma-gelatin coated flasks performed as described by Steplewski, et al. (*Science*, 221:865, 1983). Natural killer cells were removed from the monocyte preparations by treatment with anti-human Leu-11b monoclonal antibody (Becton & Dickinson, Mountain View, CA), using a concentration of 0.5 ug/ml and rabbit complement.

B. Immunization and Production of Hybridomas

BALB/c mice were immunized intraperitoneally with $3 \times 10^7$ cells of metastatic melanoma SK MEL 23 cell culture, and boosted intravenously four weeks later with $2 \times 10^6$ cells. Three days later, spleen cells were fused with the 653 variant of mouse melanoma P3X63 Ag8. The growth, cloning and maintenance of the hybridomas produced was a prescribed by Koprowski, et al. (*Somatic Cell Genetics*, 5:957, 1979). Monoclonal antibodies produced by the various hybridomas were screened using serum-free culture supernatants (Thurin, et al., *Journal of Biological Chemistry*, 260:14556, 1985) from various melanomas and cancer cell cultures. Monoclonal antibody was purified as described by Lubeck, et al. (*Journal of Immunology*, 135:1299, 1985). Hybridoma class-switch variants were produced using the procedures described by Steplewski, et al. (*Proceedings of the National Acedamy of Sciences, U.S.A.*, 82:8653, 1985).

The screening of the hybridomas for monoclonal antibodies of interest was initially performed by measuring binding to serum-free culture supernatants from cell cultures as indicated in FIG. 3. As shown in this figure, all cultures tested release the antigen into the medium. The cell cultures established from metastatic melanoma released slightly higher amounts of antigenic material than those established from primary melanoma. Non-melanoma cell cultures which did not release any of the antigens were: SW 1783 and SW 1088 astrocytoma, SW 620, SW 707, SW 1116 and SW 1345 colorectal carcinoma, KATO III gastric carcinoma, Capan-2 pancreatic carcinoma, 2774 and CaOV 3 ovarian carcinoma, T-24 bladder carcinoma, SW 75568 cervical carcinoma, Raji and MOLT lymphoblastoid, HL-60 and K 562 leukemia, SW 648 sarcoma, Tera 1 teratocarcinoma and WI 38 fibroblasts.

C. Glycolipids

Total non-alkali-treated melanoma cell ganglioside fractions were prepared as described by Herlyn, et al. (*Cancer Research*, 45:5670, 1985). The purification and characterization of gangliosides was performed essentially as described by Thurin, et al. (*Journal of Biological*

Chemistry, 260:14556, 1985). Thin-layer chromatography (TLC) was performed using glass-backed and alumina-backed highpressure TLC plates (Bodman Chemicals, Gibbstown, NJ). The solvent system used for developing the TLC plates was chloroform/methanol/0.2% $CaCl_2$ in $H_2O$ (60:40:9, V/V/V), and detection of the various fractions was done using the resorcinol reagent (Herlyn, et al., *Cancer Research*, 45:5670, 1985).

EXAMPLE 2

IDENTIFICATION OF THE ANTIGEN DETECTED BY MONOCLONAL ANTIBODY ME361

Figure 1:
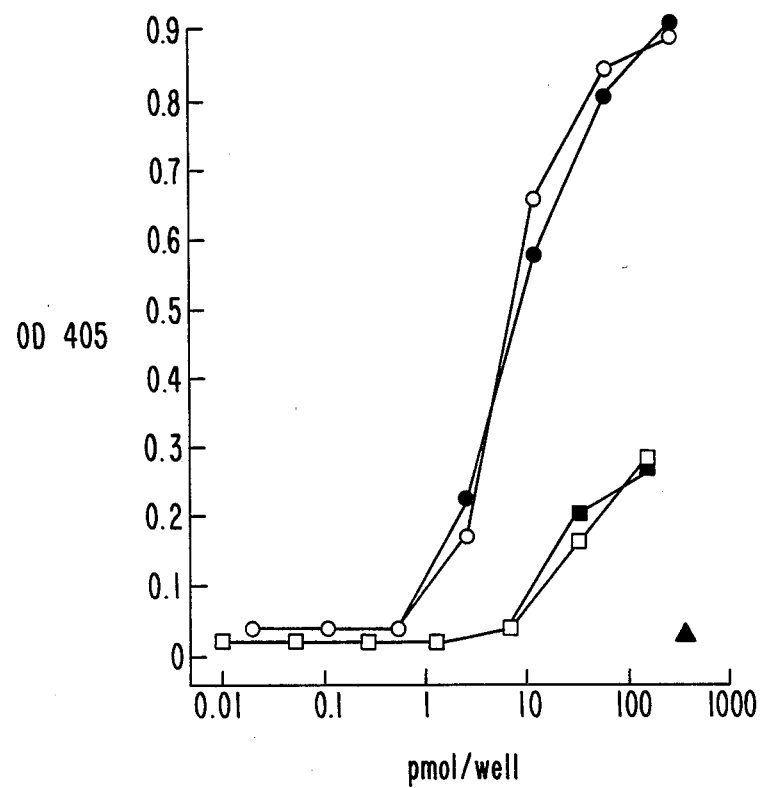
FIG. 1. Graph showing the reactivity of monoclonal antibody ME 361-S2a (ATCC HB 9326) and ME 361 (ATCC HB 9325) to serially diluted ganglioside antigens.

Solid-phase enzyme-linked immunosorbent assay (ELISA) and radioimmunoassay (RIA), were preformed in 96-well microtiter plates (Linbro/Titertek, Flow Laboratories, McLean, VA for ELISA and Dynatech Laboratories, Inc., Alexandria, VA for RIA) with purified monoclonal antibody ME 361 (1 ug/ul) and ME 361-S2a (1 mg/ml) with serially diluted ganglioside antigens. Gangliosides were serially diluted in methanol and applied to the plate in a volume of 50 ul/well. Four samples of each dilution were tested in ELISA (Thurin, et al., ibid) after evaporating the methanol at 22° C. and in RIA using $^{125}$I-labeled goat anti-mouse $F(ab')_2$ (1500 cpm/ul) as second antibody (Hansson, et al., *Journal of Biological Chemistry*, 258:4019, 1983). For all values the standard deviation was less than 7%. The results of ELISA testing indicated that higher binding levels of ME 361 and ME 361-S2a were for ganglioside GD2 followed by ganglioside GD3 (FIG. 1). ME 361 and ME 361-S2a showed essentially no reactivity with gangliosides GM4, GM3, GM2, GM1, GD1a, GD1b, GT1a, GQ 1b, and disialoparagloboside ($III^2$(Neu Ac)$_2$nLC$_4$Cuer).

The TLC binding assay was performed essentially as described by Magnani, et al. (*Methods in Enzymology*, 83:235, 1983), using hybridoma culture supernatants as a source of antibody and the same second antibody as above. Results from negative reference glycolipids (500 ng/band) were obtained from the chromatogram binding assay, except GM1, which was run serially diluted in ELISA, and plotted for simplicity (FIG. 1).

Western blotting and immunoprecipitation using extracts and cells, respectively, from melanoma cell cultures WM 75, WM 373, WM 115, WM 266-4, WM 164, and SK MEL 23, revealed no glycoprotein antigens forms associated with antibody ME 361 (data not shown).

Figure 2A:
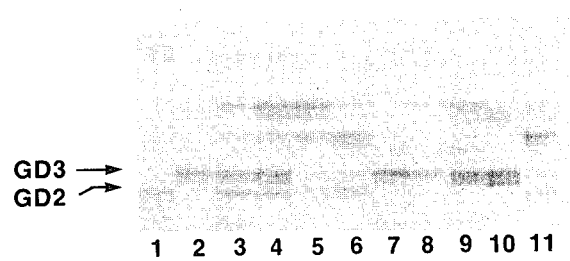
Figure 2B:
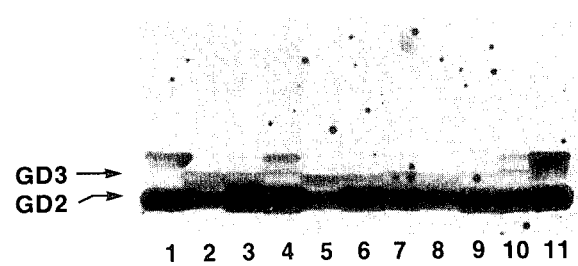
Figure 2C:
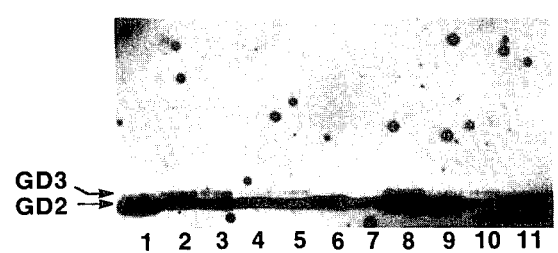

Total glycolipid fractions from human brain and erythrocytes indicated that there was no reaction with other gangliosides using the chromatogram binding assay (TLC). As shown in FIG. 2B, antibody ME 361 was shown to bind to the GD2 ganglioside (lower arrow) and also the GD3 ganglioside (upper arrow), consistent with the ELISA data. The fastest migrating bands, seen most clearly in lanes 1, 4 and 10-11 in FIG. 2B, disappeared after treatment with alkali (FIG. 2C). This indicates that in all likelihood it is the presence of lactones on GD2 that are reactive with monoclonal antibody ME 361. Monoclonal antibody ME 361 was capable of binding to total ganglioside fractions from all eleven melanoma cell cultures studies (FIG. 2, B and C).

EXAMPLE 3

TISSUE SPECIFICITY OF MONOCLONAL ANTIBODY ME 361

The reactivity of a monoclonal antibodies of the invention with cryostat sections of freshly frozen melanocytic lesions, fixed as described by Ross, et al. (*Proceedings of the National Academy of Sciences, U.S.A.*, 81:6681, 1984), was determined using the peroxidase-antiperoxidase procedure for immunoperoxidase assays (Ortho Diagnostic Systems Inc., Raritan, NJ). The binding of monoclonal antibodies to antigen present in supplemental serum-fre culture supernatants was determined by indirect solid-phase RIA (Thurin, et al., Ibid). Western blotting and immunoprecipitation were performed as described by Laemmli (*Nature*, (London), 227:680, 1970). The binding of monoclonal antibody ME 361 to tissues representing all stages of melanoma tumor progression (Clark, et al., *Human Pathology*, 15:1147, 1985) using immunoperoxidase staining on frozen cryostat sections is shown in Table 2.

TABLE 2

| IMMUNOPEROXIDASE STAINING ON FROZEN SECTIONS WITH ME 361 | | | |
|---|---|---|---|
| Tissues | Number of cases | Number of positive cases | % Positive |
| Melanocytes/keratinocytes nerves Langerhans cells | 71 | 0 | 0 |
| Nevi | 7 | 4 | 57 |
| Dysplastic nevi | 51 | 19 | 37 |
| Primary melanoma | 10 | 6 | 60 |
| Metastatic melanoma | 23 | 22 | 96 |
| Lymphocytes[a] | 126 | 23 | 18 |
| Brain | 1 | 1 | 100 |
| Pancreas | 1 | 0 | 0 |
| Liver, kidney, testis | 1[b] | 0 | 0 |

[a]Lymphocytes in sections of melanocytic lesions.
[b]One case each.

Cellular staining was diffused throughout the cytoplasm. In general, the reactivity was moderate to strong in intensity, involving 50% or more of the lesional cells in most instances. The reactivity to brain was mainly confined to myelin. Pripheral nerves were non-reactive throughout all tissues studied. The binding of ME 361 to all ganglioside fractions in FIG. 2 and all cells in Table 2 was consistent with high binding to primary and metastatic melanoma.

EXAMPLE 4

FLOW CYTOMETRIC CELL BINDING OF MONOCLONAL ANTIBODY ME 361 AND ME 361-S2a

For flow cytometry of the melanoma cell cultures, cells from one 75 $cm^2$ were trypsinized on the day before assay and transferred to a new flask. Cells were removed from the flask on the day of assay by a short incubation with 0.1% EDTA in phosphate-buffered saline and resuspended in Hanks' medium (GIBCO Laboratories, Grand Island, NY) containing 10% heat-inactivated human serum. Viability was assessed using the trypan blue exclusion technique and was found to be greater than 90%. Cells were then diluted to $4 \times 10^6$ cells/ml, and 250 ul ($1 \times 10^6$ cells) placed in a 1.5 ml Eppendorf tube for each assay. Primary antibody (50 ul) was then added and incubated for 30 minutes on ice. Undiluted culture supernatant of the mouse myeloma P3X63 Ag8 was used as a negative control. Cells were washed twice, resuspended, and incubated for 30 minutes in 50 ul of fluorescein-labeled goat anti-mouse F(ab')$_2$ diluted 1/100 (Cappel, Worthington, P.A.) in Hanks' medium as above. Cells were then washed twice and resuspended in 0.5 ml of Hanks' medium and kept on ice for less than 2 hours before flow cytometry. An Ortho Cytofluorograf 50 HH connected to a Data General MP/200 microprocessor was used (Ortho Instruments, Westwood, MA) for cytometric determinations. Cells were considered positive when their fluorescence intensity exceeded the threshold at which 99% of the cells treated with nonreactive control antibody (negative control) had lower fluorescence intensity.

The results obtained from monoclonal antibody ME 361 (ATCC HB 9325) and ME 361-S2a (ATCC HB 9326) binding using indirect flow cytometry indicated that binding had occurred to all six cell cultures which were tested (Table 3). ME 361 has isotype gamma-3 and ME 361-S2a has isotype gamma-2a.

TABLE 3

BINDING OF ANTIBODY ME 361 AND ME 361-S2a TO MELANOMA CELL CULTURES IN INDIRECT FLOW CYTOMETRY

| Cells | Antibody[a] | Mean % total binding (number of determinations) | MCF[b] |
|---|---|---|---|
| WM75 | P3 | 2.7(2) | |
| | 2a | 30.1(2) | 83 |
| | 3 | 36.0(2) | 76 |
| WM 373 | P3 | 3.8(2) | |
| | 2a | 11.2(3) | 118 |
| | 3 | 16.1(2) | 138 |
| WM 115 | P3 | 1.6(2) | |
| | 2a | 74.2(2) | 94 |
| | 3 | 80.0(1) | 90 |
| WM 266-4 | P3 | 2.5(2) | |
| | 2a | 91.6(3) | 142 |
| | 3 | 96.4(2) | 172 |
| WM 164 | P3 | 1.2(3) | |
| | 2a | 5.6(2) | 45 |
| | 3 | 16.2(2) | 57 |
| SK MEL 23 | P3 | 2.3(3) | |
| | 2a | 80.6(4) | 141 |
| | 3 | 93.9(2) | 162 |

[a]P3, culture supernatant from mouse myeloma 3X63-Ag8; 2a, 10 ug/ml of purified ME 361-S2a antibody; and 3, ME-361 containing ascites diluted 1/100.
[b]MCF, mean channel fluorescence.

The cells with the highest extractable amount of the GD2 ganglioside, that is, WM 75, WM 115, WM 226-4, and SK MEL 23 showed higher levels of antibody binding than cultures WM 373 and WM 164, which contain relatively small amounts of GD2. However, WM 373 and WM 164 cells had sufficient amounts of the GD3 ganglioside, so that despite weak antibody reactivity to GD3 (FIG. 1), these cultures were still capable of binding ME 361 and ME 361-S2a (Table 3). Other melanoma cell cultures which were also reactive with monoclonal antibody ME 361 and ME 361-S2a were WM 9, WM 46, and the neuroblastoma cell culture IMR-5.

EXAMPLE 5

CYTOTOXICITY OF ME 361 AS MEASURED BY ANTIBODY DEPENDENT CELL CYTOTOXICITY (ADCC) AND COMPLEMENT DEPENDENT CYTOTOXICITY (CDC)

ADCC was measured using an 18 hours $^{111}$In release assay. In the assay ascites fluid was used at a 1/100 dilution, which was the highest dilution giving significant lysis in the assay, as titered on melanoma cell culture WM 164. No attempts were made to compare the killing efficiency of the two different ME 361 isotypes, since the purified gamma-3 antibody (ME 361) was difficulty to solubilize at the necessary concentrations. However, purified gamma-2a monoclonal antibody (ME 361-S2a) at a concentration of 10 ug/ml showed the same effect as the 1/100 ascites fluid dilutions. Target cells ($1 \times 10^6$) were labeled with 10 uCi of [$^{111}$In] indium oxine (Medi-Physics Inc., Emeryville, CA) for 15 minutes in 15 ul of saline at 21° C. The cells were washed three times in medium and were added at $1 \times 10^4$ cell/well in roundbottom microtiter plates (Linbro, Flow Laboratories, McLean, VA). In the ADCC assay, effector cells and various concentrations of a monoclonal antibodies were added in triplicate and incubated for 18 hours at 37° C. in 5% CO$_2$. Plates were then centrifuged at 80 g for two minutes. The supernatants were harvested and analyzed using a gamma-counter. The percentage cytotoxicity was calculated by the following formula:

$$\% \text{ cytotoxicity} = \frac{\text{experimental } CPM - \text{spontaneous } CPM}{\text{input } CPM - \text{spontaneous } CPM} \times 100$$

The values obtained are shown in Table 4 and reflect those numbers obtained after control values have been substracted (%$^{111}$In release without monoclonal antibody ME 361 or ME 361-S2a). A standard deviation in these determinations was below 10% for all values.

TABLE 4

ADCC AND CDC AGAINST SIX MELANOMA CELL CULTURES IN $^{111}$ IN RELEASE ASSAY

| Cells | Antibody ME 361 isotype | Monocytes[a] | | Lymphocytes[a] | | CDC |
|---|---|---|---|---|---|---|
| | | #1[b] | #2 | #1 | #2 | #1 |
| WM 75 | 3 | 48.3[c] | 41.1 | 28.5 | 35.1 | 49.3 |
| | 2a | 36.4 | 29.9 | 30.1 | 35.1 | 24.7 |
| WM 373 | 3 | 22.8 | 15.5 | 17.4 | 19.2 | 15.1 |
| | 2a | 12.4 | 7.2 | 6.7 | 7.9 | 2.8 |
| WM 115 | 3 | 27.6 | 21.8 | 19.1 | 21.7 | 19.1 |
| | 2a | 15.6 | 9.4 | 7.4 | 15.8 | 1.1 |
| WM 266-4 | 3 | 29.8 | 27.6 | 24.7 | 24.4 | 46.1 |
| | 2a | 17.6 | 13.7 | 12.1 | 24.3 | 7.2 |
| WM 164 | 3 | 29.8 | 30.4 | 13.1 | 26.2 | 36.2 |
| | 2a | 12.3 | 14.5 | 6.7 | 15.2 | 15.2 |
| SK MEL 23 | 3 | 48.9 | 34.4 | 35.7 | 32.0 | 59.9 |
| | 2a | 41.3 | 26.6 | 22.2 | 35.3 | 64.6 |

[a]Effector-to-target cell ratio is 50:1.
[b]Indicates donors of peripheral blood lymphocytes.
[c]Expressed as % cytotoxicity above background which in no case was higher than 10% in ADCC and 6% in CDC.

For the CDC assay, the $^{111}$In-labeled target cells were incubated in microtiter plates with 40% autologous plasma from human donors and various concentrations of monoclonal antibodies.

In evaluating the ADCC and CDC activity of ME 361 and ME 361-S2a six melanoma cell cultures were selected which had different ganglioside patterns. These cell cultures are described in Table 1. All cells were significantly lysed in ADCC when human monocytes and lymphocytes, using an effector-to-target cell ratio of 50:1, as well as in CDC with complement in an 18 hours $^{111}$In release assay (Table 4). The killing efficiency of ME 361 and ME 361-S2a was significantly higher (p 0.01, Student's T-test, using all four values) for WM 75 cells than for WM 373 cells. This finding is consistent with the greater concentration of GD2 and higher antibody binding levels in the WM 75 cells.

However, no significant difference was found between the lysis of WM 115 and WM 266-4 cells (derived from a single individual), which correlated well with the similar ganglioside patterns of these cultures. Antibody binding in the direct flow cytometry assay, described supra, was also similar for WM 115 and WM 266-4 cells, that is, 73% and 83% (Table 3), respectively. The distribution of the major gangliosides GM3, GM2, GD3 and GD2 in these cell cultures were similar, in sharp contrast with the pattern seen for WM 75 cells, in which GD2 was the major ganglioside, and for WM 373 cells, in which GD3 was the major ganglioside and GD2 was found only in low amounts (FIGS. 2, A and B, lanes 1–4). In the case of two cell cultures from different individuals, monoclonal antibody binding and killing of cells expressing both GD2 and GD3 (SK MEL 23) was greater than in cells expressing only GD3 (WM 164).

The invention now being fully described, it will be apparent to one of ordinary skill in the art that many changes and modifications can be made without departing from the spirit or scope of the invention.

We claim:

1. A continuous hybridoma cell line capable of secreting monoclonal antibodies reactive with ganglioside antigens GD2 and GD3 and is essentially non-reactive with other ganglioside antigens.

2. The hybridoma of claim 1, wherein said hybridoma is selected from the group consisting of ATCC HB 9325 and ATCC HB 9326 and their isotype switch variants.

3. A monoclonal antibody reactive with ganglioside atigens GD2 and GD3, wherein said antibody is preferentially reactive with GD2 and is essentially non-reactive with GQ 1b.

4. The monoclonal antibody, according to claim 3, wherein said monoclonal antibody is produced by a cell line selected from the group consisting of ATCC HB 9325 and ATCC HB 9326.

5. The monoclonal antibody according to claim 3 having the specificity of a monoclonal antibody produced by hybridoma cell line ATCC HB 9325.

* * * * *